United States Patent [19]

Warchol

[11] Patent Number: 4,685,325
[45] Date of Patent: Aug. 11, 1987

[54] MEASUREMENT OF GAS CONTENT IN MOLTEN METAL USING A CONSTANT CURRENT SOURCE

[75] Inventor: Mark F. A. Warchol, New Kensington, Pa.

[73] Assignee: Aluminum Company of America, Pittsburgh, Pa.

[21] Appl. No.: 825,344

[22] Filed: Feb. 3, 1986

[51] Int. Cl.$^4$ ............................................. G01N 27/18
[52] U.S. Cl. ........................................ 73/19; 73/1 G; 73/27 R
[58] Field of Search .......................... 73/19, 1 G, 27 R

[56] References Cited

U.S. PATENT DOCUMENTS 2,861,450  11/1958  Ransley .................................... 73/19
4,454,748   6/1984  Teral et al. .............................. 73/19

Primary Examiner—Stewart J. Levy
Assistant Examiner—Joseph W. Roskos
Attorney, Agent, or Firm—Elroy Strickland

[57] ABSTRACT

A single catharometer cell is employed in combination with a source of DC voltage and a device that provides constant electrical current for the cell. The constant current source provides a fixed reference for balancing against the electrical current flow through the cell when the cell contains only a carrier gas. An operational amplifier is connected across the cell and is adjustable to provide a desired output when a known amount of a second gas is present in the cell.

3 Claims, 1 Drawing Figure

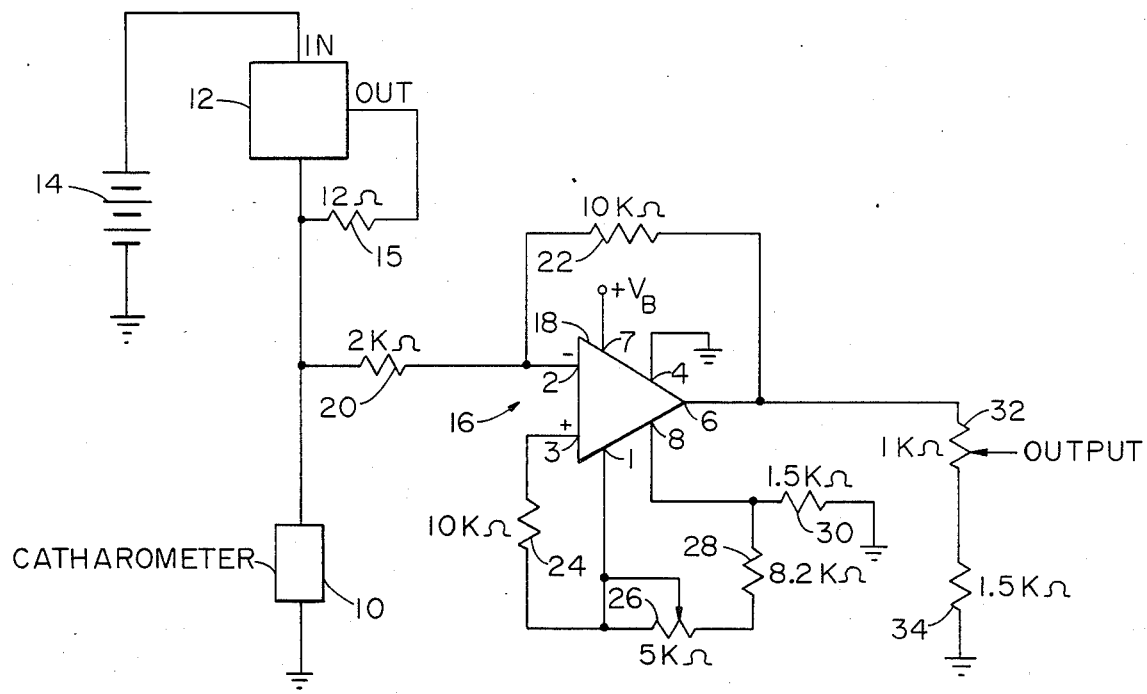

MEASUREMENT OF GAS CONTENT IN MOLTEN METAL USING A CONSTANT CURRENT SOURCE

BACKGROUND OF THE INVENTION

The present invention is related generally to apparatus for determining the amount of soluble gas contained in a body of molten metal, and particularly to an electrical circuit arrangement that greatly simplifies and reduces the cost of the circuit arrangement presently employed by such apparatus. In addition, the circuit arrangement of the invention considerably reduces the consumption of power.

U.S. Pat. 2,861,450 to Ransley and pending U.S. Patent application Ser. No. 763,290 to Warchol et al, (Warchol being the inventor of the present invention), disclose apparatus employed to measure the amounts of soluble gases found in molten aluminum and aluminum alloys, hydrogen being the most important of these gases. The disclosures of Ransley and Warchol et al are incorporated herein by reference. Both disclosures employ a catharometer comprises of two cells, with each cell including a fine platinum wire coil electrically connected in two legs of an electrical resistance bridge circuit. A small electrical potential is applied across the bridge and cells to heat the platinum wires. Each of the cells includes a structure for housing the wire, one of which is opened to atmosphere, such that the cell receives a relatively constant amount of hydrogen gas and therefore serves as a reference cell. The other cell is a measuring cell and has its housing connected to receive a carrier gas containing molecules of a second, hydrogen gas, for example, that is soluble in molten metal. The hydrogen constant of the reference cell is balanced against the carrier gas in the measuring cell before the carrier gas receives molecules of the hydrogen gas to obtain a zero value indicative of such balance. This balancing requires identical platinum wire elements which are generally handwound on inert insulating cores. The winding process is a tedious, time consuming process which ultimately does not guarantee that the matching process will be correct.

In addition, it can be appreciated that a resistance bridge circuit, which includes the platinum wires, requires, i.e., consumes, a certain amount of electrical energy. Apparatus employed for determining soluble gas content are portable, as they must be moved from furnace to furnace to make the measurements discussed above. For this reason such apparatus are battery powered. Hence, the importance of minimum power consumption.

SUMMARY OF THE INVENTION

The present invention involves the discovery that the reference catharometer cell can be eliminated along with the bridge circuit by use of an inexpensive solid-state constant current source (as opposed to a constant voltage source) to provide the reference for comparison with the electrical resistance of a single catharometer cell. The constant current source is connected in electrical series between a battery and the single cell. Pure carrier gas is introduced into the cell (and system) to purge the same, as discussed in the Warchol et al application. The presence of the carrier gas stablizes the electrical resistance of the wire. This stabilizes the flow of electrical current through the wire and the resulting drop in the voltage developed across the wire. An operational amplifier is connected across the catharometer wire to provide a voltage buffer with gain, that increases the sensitivity of the reading provided by the catharometer. A zero offset voltage reference is provided that allows adjustment of the amplifier output. In this manner amplifier output can be nulled to zero volts or another predetermined voltage value.

The carrier gas is circulated through the body of molten metal such that it entrains molecules of the gas (hydrogen) dissolved in the molten metal. The two gases are then directed to the cell, which cools the platinum wire and decreases its electrical resistance, i.e., hydrogen has a greater ability to remove heat from the wire of the cell than that of the carrier gas, which may be nitrogen, for example. The voltage drop across the wire is now changed from that existing across the amplifier; the voltage drop across the wire being proportional to the hydrogen content of the carrier gas. The amplifier now provides an output that is a reading of the amount of hydrogen in the body of molten metal.

THE DRAWING

The invention, along with its objectives and advantages, will be best understood from consideration of the following detailed description and accompanying drawing, the sole FIGURE of which is a schematic representation of the circuit of the invention.

PREFERRED EMBODIMENT

Referring now to the drawing, a catharometer cell 10 is shown schematically, and is shown connected between ground and a constant current source 12. The cell, as discussed above, includes a single coil of platinum wire (not shown) that serves to measure the amount of gas content in a body of molten metal (not shown). Hence, the wire is contained in a housing (not shown) to receive the gas content. It is believed unnecessary to show further details of the apparatus, as such are depicted and described in the above references to Ransley and Warchol et al.

Constant current source 12 is connected in electrical series between cell 10 and a direct current (battery) source 14. The constant current source is preferably a compact, low current drain, solid-state device, for example, such as the LM317 available from National Semiconductor of Santa Clara, Calif., though devices are available and can be used. The LM317 is a three terminal (pin) adjustable voltage regulator that is ordinarily used, as the name indicates, to regulate voltage. The device, however, can be made to regulate current and thereby provide a constant supply of current. This is accomplished by connecting a resistor 15 between an output pin of the device and and "adjustable" pin of the device. The adjustable pin and resistor gives the device the flexibility employed here. A twelve ohm resistor, for example, provides a constant direct current (DC) output from device 12 of 104 milliamps. Any call for a change in current from 12 is compensated for by the device, the change appearing between the input and output terminals as a change in voltage, as opposed to appearing across resistor 15. A 104 milliamp supply is suitable for the purposes of the present invention.

Connected across cell 10 is "balancing" circuit 16. Circuit 16 is employed to balance the current flow through cell 10, when carrier gas alone is present in the cell, against the constant current supply provided by current source 12. In this manner, when the carrier gas is circulated in the molten metal, and hydrogen gas is entrained in the carrier gas, the voltage change developed across cell 10 will be proportional to the amount of hydrogen in the carrier gas and thus in the molten metal. Preferably, circuit 16 is that of an operational amplifier, designated 18, though other circuit means can be employed. An amplifier that has been found suitable for the purposes of the invention is National's eight pin LM10.

The voltage drop across cell 10 is shown directly coupled to the negative input (pin 2) of amplifier 18 via a two thousand ohm resistor 20. The gain of the amplifier is fixed by an external feedback resistor 22 connected between pin 2 and 6, which is a 10K ohm resistor if the LM10 is employed in the manner shown in the drawing.

The LM10 is a combination of two operational amplifiers with pins 1 and 8 being the terminals of the second amplifier. Pins 2, 3, and 6 are those of the first amplifier. The positive terminal (pin 3) of the first amplifier is connected to the output (pin 1) of the second amplifier via a 10K resistor 24 such that the positive input to the first amplifier is the output of the second amplifier. In this manner, the first amplifier is under the control of the second amplifier, as explained in detail hereinafter.

Pin 8 is the input terminal of the second amplifier. The gain of the second amplifier is set by a 5K ohm adjustable feedback resistance 26 and a fixed, 8.2K ohm feedback resistor 28. The input impedance for the second amplifier is established by 1.5K ohm resistor 30 when using (again) the LM10 amplifier.

The output voltage (pin 6) of amplifier 18 is developed across an adjustable 1K ohm resistance 32 and a fixed 1.5K resistor 34, 34 providing an appropriate range of adjustment for 32.

The apparatus and circuit, as thus far described, functions in the following manner. The catharometer 10, along with a probe and associated plumbing, as described in the above patent references, is purged with an inert carrier gas. Current flow through cell 10 stabilizes, as the electrical resistance of the platinum wire coil of 10 stabilizes in the process of the gas withdrawing heat from the coil; it will be recalled that the coil of cell 10 is heated by current flow from battery 14 and current source 12.

With current flow through cell 10 now stable, the voltage drop across the cell and thus the voltage applied to the negative input of amplifier 18 is stable. Any output at pin 6 resulting from the voltage applied by cell 10 is now made zero by adjusting resistance 26, i.e., the voltage input of 18 at pin 3 is made equal to that developed across cell 10. Resistor 28, connected in series with 26, establishes an appropriate range of adjustment for 26 such that the output of 18 (at pin 6) can be zeroed in terms of the voltage value applied to pin 2.

With the circuit of 16 now zeroed, the purge-carrier gas is next directed to the body of molten metal. As explained in the above references to Ransley and Warchol, the carrier gas acquires molecules of the gas content of the molten metal and carries the same to cell 10. This process continues until the pressure between the two gases reaches equilibrium. The presence of the gas content (hydrogen, for example) in cell 10 changes the resistance of the platinum wire by cooling the same, as the gas content (hydrogen) has a greater capacity for removing heat from the wire than the carrier gas. The voltage drop across cell 10 is now changed from that existing across circuit 16 such that 16 now outputs a signal at pin 6 of 18 that is a reading of the proportionality of the gas content to the carrier gas. This reading, as explained in the Warchol application, is used to determine the gas content of the body of molten metal. The constant current provided by source 12 assures a voltage drop across cell 10 that changes only in response to the precise amount of gas content in cell 10.

In making wire coils for cell 10, the physical lengths of the wires may not always be the same such that slight differences in electrical resistances can occur from coil to coil. To care for this, and thereby insure accurate readings of gas content when a new coil is prepared and used, circuit 16 is provided with a "span adjustment" in the presence of adjustable resistance 32. A known, predetermined amount of gas content, say 6 percent hydrogen, is combined with the carrier gas, such that the remainder (94 percent) is carrier gas. With appropriate adjustment of resistance 32 circuit 16 is provided with a desired known output at pin 6. This adjustment calibrates the circuit of 16 for the particular platinum wire that will be used to determine the amount of gas content in bodies of molten metal.

From the above description it can be appreciated that the use of a single catharometer cell and a source of constant current provide efficiencies heretofore unattainable in apparatus for determining soluble gas content, including a substantial reduction in current requirements, as the bridge circuit of such apparatus and the second (reference) cell are eliminated.

While the invention has been described in terms of preferred embodiments, the claims appended herto are intended to encompass all embodiments which fall within the spirit of the invention.

What is claimed is:

1. In combination;
    a single catharometer cell adapted to receive a carrier gas and a second gas dissolved in a body or flow of molten metal, and to measure equilibrium between the two gases,
    a source of DC voltage,
    means providing constant electrical current for said cell electrically connected between the cell and the source of DC voltage, and
    means for balancing electrical current flow through the cell when the cell contains only the carrier gas against said constant electrical current.

2. The combination of Claim 1 including
    an operatonal amplifier electrically connected to the constant current source and across the cell, and
    means for zeroing the output of the amplifier,
    said zeroing means being the means that effect the current balancing of the cell against the constant current source when the cell contains only the carrier gas.

3. The combination of Claim 2 including means for adjusting the operational amplifier to provide a desired amplifier output when a known amount of the second gas is present in the cell.

* * * * *